United States Patent [19]

Miki et al.

[11] Patent Number: 4,803,866

[45] Date of Patent: Feb. 14, 1989

[54] AIR-FUEL RATIO DETECTING DEVICE

[75] Inventors: Masayuki Miki, Katsuta; Seikou Suzuki, Hitachioota, both of Japan

[73] Assignee: Hitachi Ltd., Tokyo, Japan

[21] Appl. No.: 45,412

[22] Filed: May 4, 1987

[30] Foreign Application Priority Data

May 8, 1986 [JP] Japan .................................. 61-105550

[51] Int. Cl.$^4$ ........................................... G01N 27/12
[52] U.S. Cl. .......................................... 73/23
[58] Field of Search ..................... 73/23, 116

[56] References Cited

U.S. PATENT DOCUMENTS

| | | | |
|---|---|---|---|
| 4,112,893 | 9/1978 | Anzai ................................... | 73/23 X |
| 4,121,548 | 10/1978 | Hattori et al. ....................... | 73/23 X |
| 4,291,572 | 9/1981 | Maurer et al. ........................... | 73/23 |
| 4,306,444 | 12/1981 | Hattori et al. ........................... | 73/23 |
| 4,344,317 | 8/1982 | Hattori et al. ........................... | 73/23 |
| 4,393,841 | 7/1983 | Drews et al. ........................... | 73/23 X |
| 4,471,648 | 9/1984 | Uchida et al. ........................... | 73/23 |

Primary Examiner—Stewart J. Levy
Assistant Examiner—Joseph W. Roskos
Attorney, Agent, or Firm—Fay, Sharpe, Beall, Fagan, Minnich & McKee

[57] ABSTRACT

A switch element ($SW_1$) is connected in series between an air-fuel ratio detecting cell (1) and a power source (Vo) and controlled by a control time generator (4). A potential ground ($V_{PG}$) is connected to a cathode side of the detecting cell (1). An output voltage from the detecting cell (1) is input into a sample hold circuit ($SW_2$, $C_1$, $A_2$) which is controlled by a control time generator (4) adapted to control the switching element ($SW_1$) and sample hold circuit alternately. An output from the sample hold circuit is compared with an electromotive force control value (e) in a comparator circuit ($A_1$), and output as an oxygen concentration-detected signal. A temperature setting resistor ($r_2$) and a load resistor ($R_2$) are connected between an output terminal of the sample hold circuit and the switching element ($SW_1$). The voltage ($e^+$, $e^-$) from a node of the detecting cell (1) and an electric current detecting resistor ($R_1$) and a node of the temperature setting resistor ($R_2$) and load resistor ($R_2$) are input into a differential amplifier ($A_3$). The electric current flowing to a heater contained in the detecting cell (1) is controlled by a transistor (Tr) on the basis of an output from the differential amplifier ($A_3$). As a result, the internal resistance of the detecting cell (1) is controlled to constant level.

26 Claims, 5 Drawing Sheets

AIR-FUEL RATIO DETECTING DEVICE

FIELD OF THE INVENTION

This invention relates to an air-fuel ratio sensor used for a combustion controlling operation, and more particularly to an air-fuel ratio detecting device suitably used for regulating the temperature of an air-fuel ratio sensor.

BACKGROUND OF THE INVENTION

The conventional air-fuel ratio sensors for detecting an air-fuel ratio from the gaseous components in an exhaust gas include, for example, "Apparatus for Measuring Partial Pressure of Predetermined Gaseous Components in Monitored Gas Environment" disclosed in Japanese Patent Laid-Open No. 69690/1977 published on June 9, 1977, and "Inflammable Substance Sensor" disclosed in Japanese Patent Laid-Open No. 66292/1978 published on June 13, 1978, in which a constant or variable voltage is applied to an air-fuel ratio detecting cell to determine the air-fuel ratio on the basis of an amperage obtained. These air-fuel ratio sensors depend much upon the temperature, so that they required to be used at a high temperature. The methods of controlling the temperature of an air-fuel ratio sensor include a method of applying a voltage, in which an AC component is superposed on a DC voltage, to a detecting cell, and controlling the temperature on the basis of the temperature dependency information from the AC component, and a method of determining the internal resistance of a detecting cell on the basis of an AC component, and controlling the temperature on the basis of the internal resistance, as disclosed in Japanese Patent Laid-Open No. 187646/1982 entitled "Method of and Apparatus for Measuring Temperature of Threshold Current Sonde or Oxygen Sonde" and published on Nov. 18, 1982, and Japanese Patent Laid-Open No. 192852/1982 entitled "Temperature-controlled Threshold Current Type Oxygen Concentration Detector" and published on Nov. 27, 1982. Japanese patent Laid-Open No. 192849/1982 entitled "Measuring Output Temperature compensated Threshold Current Type Oxygen Concentration Detector" and published on Nov. 27, 1982 discloses a method in which the steps of applying a voltage to a detecting cell to measure a threshold current, and determining the internal resistance are repeatedly carried out. In this method, the signal processing is done by determining a temperature compensation factor, and then carrying out computations.

However, in the conventional air-fuel ratio sensors, in which the detection of an air-fuel ratio and the obtaining of temperature information are carried out on the basis of a DC component and an AC component, respectively, it is necessary that the AC component superposed on the DC component so as to obtain an air-fuel ratio output from the air-fuel ratio sensors be separated therefrom. This makes it necessary to provide a special signal processor or computing element.

Japanese Patent Laid-Open No. 163862/1982 entitled "Detecting Circuit for Oxygen Concentration Sensor" and published on Oct. 8, 1982 discloses a circut structure for outputting a signal representative of the possibility that the detecting cell will be normally operated, on the basis of the internal resistance of a detecting cell, and outputting a signal received from the detecting cell. However, the controlling of the temperature of a detecting cell is not disclosed in the conventional circuit.

SUMMARY OF THE INVENTION

An object of the present invention is to provide an air-fuel ratio detector capable of detecting an air-fuel ratio and controlling a temperature on the basis of a DC component alone, and preventing a decrease in the air-fuel ratio detecting accuracy based on the internal resistance of the detecting cell, and the output oscillation at the time of entry into an electron conduction region, without providing any special signal processor.

According to the present invention, which will be understood clearly from the description to be given later, a bridge circuit which uses the electromotive force of an air-fuel ratio detecting cell in one arm of the bridge circuit is formed, and a heater contained in the air-fuel ratio detecting cell is controlled on the basis of a difference in the electric potentials at the output terminals of the bridge circuit to thereby regulate the temperature of the air-fuel ratio detecting cell to a predetermined level.

Owing to this structure, a decrease in the detecting accuracy, which is ascribed to a voltage drop due to the internal resistance of the air-fuel ratio detecting cell, and the occurrence of output oscillation can be prevented.

DETAILED DESCRIPTION OF THE PREFERRED EMBODIMENTS

Figure 1:
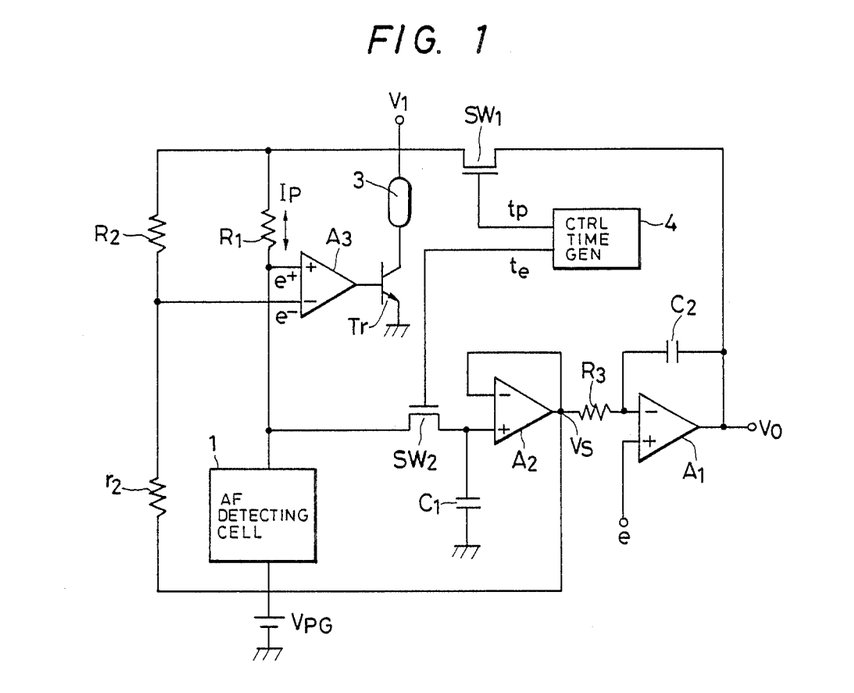
FIG. 1 is a construction diagram of a basic circuit in the present invention.

The reference numerals and letters in FIG. 1 denote the following, i.e., 1 an air-fuel ratio detecting cell, $A_1 A_2$, $A_3$ differential amplifiers, SW1, SW2 switches adapted to be turned on and off electrically, $R_1$, $R_2$, $R_3$, $r_2$ resistors, $C_1$, $C_2$ capacitors, 3 a heater, 4 a control time generator, e an electromotive force control value, $V_{PG}$ potential ground, Tr a transistor, a $V_0$ an output voltage.

Figure 2A:
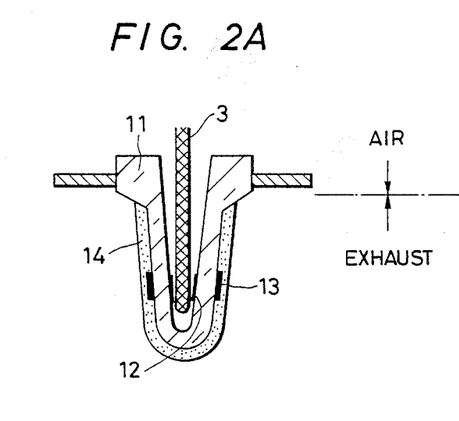
FIG. 2A is a schematic construction diagram of a bottomed tube type air-fuel ratio detecting cell used in the present invention.
Figure 2B:
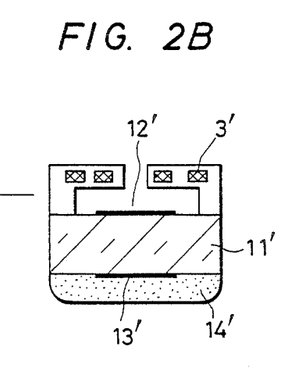
FIG. 2B is a schematic construction diagram of a plate type air-fuel ratio detecting cell made by a thick film process and a thin film process.

Referring to FIG. 2, reference numerals 11, 11' denote solid electrolytes of zirconia, 12, 12' atmospheric air-contacting platinum electrodes, 13, 13' exhaust gascontacting platinum electrodes, 14, 14' gas-diffusing resistors, and 3, 3' built-in heaters, and the parts of either type of detecting cell can be used in the present invention. The detection of an air-fuel ratio is carried out by utilizing the oxygen pumping phenomenon and electromotive force characteristics of the solid electrolyte of zirconia.

In the air-fuel ratio detecting cell 1, such a gradual electromotive force E that has substantially zero volts in a lean (excess air ratio $\lambda > 1$) region which is on one side of a line of $\lambda = 1$, and about one volt in a rich ($\lambda < 1$) region which is on the other side of this line, as known well by the following Nernst's equation (1).

$$E = (RT/4F)\ln(Pa/Pe) \qquad (1)$$

wherein F is the Faraday constant, R a gas constant, T an absolute temperature, Pa the concentration of the oxygen in the atmospheric air, and Pe the oxygen concentration on the exhaust gas-side electrode interface. The chemical reaction formula for this case is as follows.

$$2CO + O_2 \rightleftarrows 2CO_2 \qquad (2)$$

Accordingly, the oxygen concentration on the exhaust gas-side electrode interface is controlled so that a predetermined electromotive force E (preferably 0.5 V) occurs in all regions of $\lambda$. Namely, by an oxygen pumping phenomenon, the oxygen on the exhaust gas-side electrode interface is discharged to the atmospheric air when $\lambda > 1$, to reduce the oxygen concentration thereon, and, conversely, the oxygen is injected frm the atmospheric air into this interface when $\lambda < 1$, to increase the oxygen concentration thereon, whereby the electromotive force E of the air-fuel ratio detecting cell is controlled to be constant. Therefore, the concentration of oxygen in the exhaust gas can be determined on the basis of the pumping amperage corresponding to the oxygen injection rate or oxygen discharge rate required to set the electromotive force E to a predetermined level. The polarities of the pumping current at $\lambda > 1$ and $\lambda < 1$ become opposite to each other. Namely, when $\lambda > 1$, a positive pumping amperage $I_p$ is attained, and, when $\lambda < 1$, a negative pumping amerage $I_p$.

Referring to FIG. 1, the control time generator 4 outputs a signal of electromotive force measuring time $t_e$ the level of which becomes high in the time zone for measuring the electromotive force of the air-fuel ratio detecting cell 1, and a signal of control time tp the level of which becomes high in the time zone for detecting the air-fuel ratio and controlling the heater. When $t_e$ is in a high level, tp is in a low level, and, conversely, when $t_e$ is in a low level, tp is in a high level.

A voltage source for an automobile is about 14 V, and positive and negative pumping currents flow through a sensor used in the present invention, so that a virtual ground higher than the earth level is required. Therefore, it is necessary that the cathode, the exhaust-side electrode, of the air-fuel detecting cell consists of a potential ground higher than the earth level. The air-fuel ratio detecting cell 1 can be denoted electrically by a equivalent circuit comprising a series circuit of electromotive force E and an internal resistance r which are not shown in the drawings.

When $t_e$ is in a high level with tp in a low level, SW2, SW1 are turned on and off, respectively, with the pumping current for th air-fuel ratio detecting cell 1 cut off. Accordingly, the sum of the electromotive force E and potential ground $V_{PG}$, i.e. the electric potential $E + V_{PG}$ occurs in the anode of the detecting cell 1, and is held in a sample/hold circuit (which will hereinafter be referred to as S/H circuit) and input into an intergrator consisting of $R_3$, $C_2$, $A_1$.

When tp is in a high level with $t_e$ in a low level, SW1, SW2 are turned on and off, respectively. In the integrator, an electromotive force control value e and a hold value Vs in the S/H circuit are compared with each other to regulate the flow rate of the pumping current through the air-fuel detecting cell 1 on the basis of a difference therebetween. When this control operation is repeated, the hold value is controlled to be Vs=e, and the concentration of the oxygen in the exhaust gas, i.e. air-fuel ratio can be determined on the basis of a threshold amperage of the pumping current Ip at this time. It is, of course, necessary that the electromotive force control value e to be set to a level determined by adding $V_{PG}$.

The controlling of the temperature of the air-fuel ratio detecting cell will now be described.

The detection of an air-fuel ratio in this embodiment is carried out by utilizing an oxygen pumping phenomenon of the solid electrolyte of zirconia as previously mentioned. Accordingly, it is necessary that the internal resistance of the zirconia be reduced, i.e., the zirconia be heated to a high constant temperature by the built-in heater.

To meet this requirement, the S/H circuit consisting of the switch SW2, capacitor $C_1$ and differential amplifier $A_2$ is connected to the bridge circuit consisting of the load resistor $R_2$ and temperature setting resistor $r_2$ in parallel with the pumping current Ip-detecting resistor $R_1$ and air-fuel ratio detecting cell 1, and the built-in heater is controlled by the differential amplifier $A_3$ so that the bridge circuit is equilibrated.

When the pumping current Ip flows with the level of the signal of the time tp for controlling the temperature of the heater high, SW1, SW2 are turned on and off, respectively. The voltage $V_L$ at the anode-side terminal of the air-fuel ratio detecting cell at this time is expressed by the following equation.

$$V_L = V_{PG} + Ip \cdot r + E \qquad (3)$$

As is clear from the equation (3), the voltages at both terminals of the air-fuel ratio detecting cell drop due to Ip, and consist of components of electromotive force, so that one side of the bridge opposed to the air-fuel ratio detecting cell 1 also requires components corresponding to Ip·r and E. Therefore, it is necessary to provide $r_2$ in opposition to r, and the output Vs of the S/H circuit in opposition to E.

Let $e^+$ and $e^-$ equal the positive input terminal voltage and negative input terminal voltage, respectively, of the differential amplifier $A_3$. The following equations can be established.

$$e^+ = \frac{[V_o - (E + V_{PG})]r}{R_1 + r} \qquad (4)$$

$$e^- = \frac{(V_o - V_s)r_2}{R_2 + r_2} = \frac{[V_o - (E + V_{PG})]r_2}{R_2 + r_2} \qquad (5)$$

The equations (4), (5) are expressed as follows in view of the stabilization conditions for the differential amplifier $A_3$.

$$\frac{[V_O - (E + V_{PG})]r}{R_1 + r_1} = \frac{[V_O - (E + V_{PG})]r_2}{R_2 + r_2} \quad (6)$$

Accordingly, if the equation (6) is reduced, the following equation can be obtained.

$$R_1/r = R_2/r_2 \quad (7)$$

Figure 4:
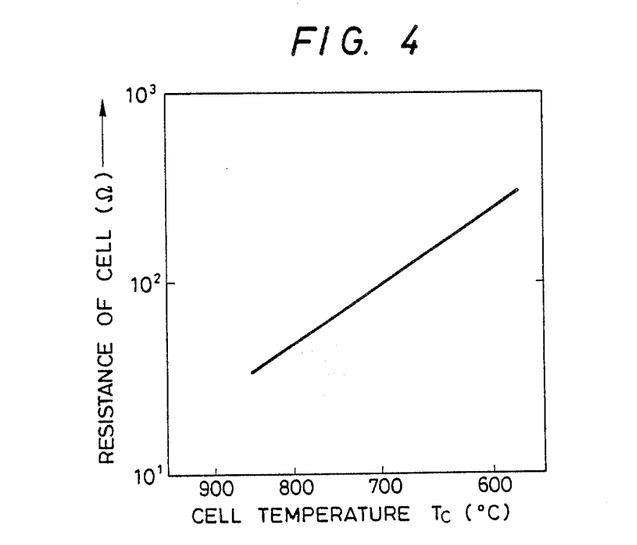
FIG. 4 is a characteristic diagram of the internal resistance of the air-fuel ratio detecting cell with respect to the temperature thereof.

Thus, the equilibration conditions for the bridge circuit are established. Therefore, if the amperage of the current supplied to the built-in heater 3 is regulated by the transistor Tr so that the equation (7) is established, the internal resistance r shown in FIG. 4 of the air-fuel ratio detecting cell 1 becomes equal to the temperature setting resistance $r_2$, so that the regulation of the temperature of the air-fuel ratio detecting cell 1 becomes possible.

Figure 3:
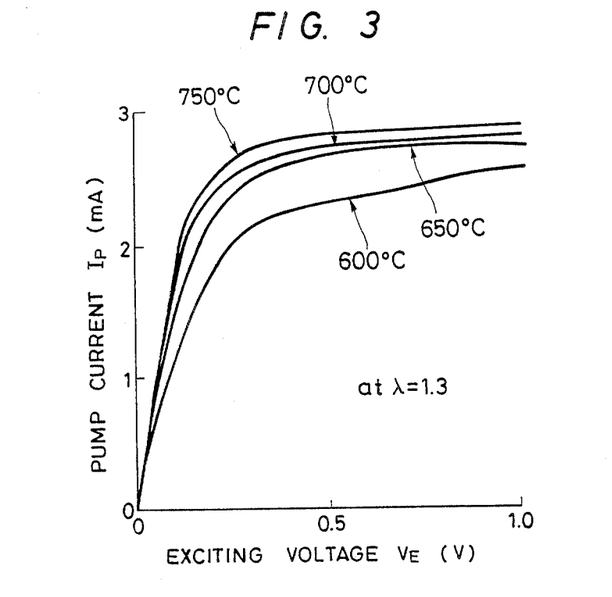
FIG. 3 is a characteristic diagram showing the temperature dependency of the pumping current with respect to the excitation voltage of the air-fuel ratio detecting cell.

Referring to FIG. 3, a threshold amperage at which the pumping current Ip becomes saturated varies depending upon the temperature. Accordingly, it is necessary that the air-fuel detecting cell 1 be heated and controlled to a high and constant temperature.

Figure 5:
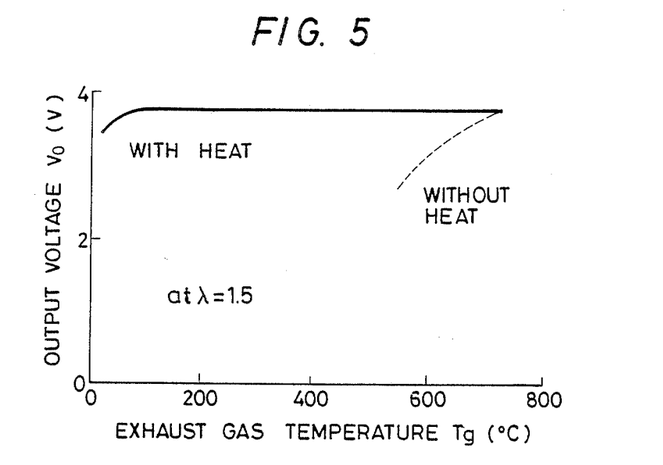
FIG. 5 is a characteristic diagram of an output voltage with respect to the temperature of an exhaust gas.

Referring to FIG. 5, a solid line shows the relation between the output voltage and exhaust gas temperature, which relation is determined in the case where the temperature of the air-fuel ratio detection cell is regulated to a high constant temperature, and a broken line the similar relation determined in the case where such regulation of the temperature is not carried out. The drawing shows that a stable output voltage can be obtained at an exhaust gas temperature of larger than about 100° C.

Figure 6:
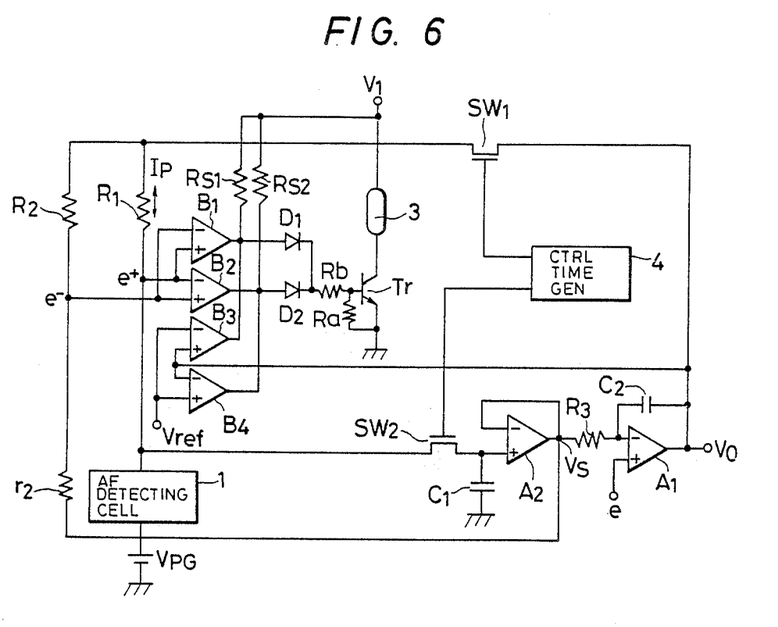
FIG. 6 shows an example of the basic circuit of FIG. 1, which enables the controlling of the temperature of the air-fuel ratio detecting cell to be done in all air fuel ratio regions.

The air-fuel ratio regions of an automobile consist of a lean region of $\lambda > 1$ on one side of a line of $\lambda = 1$, and a rich region of $\lambda < 1$ on the other side of the line, and the polarities of the pumping current Ip reverse in these regions as previously mentioned. Therefore, in order to control the temperature stably in all air-fuel ratio regions, two input signals $e^+$, $e^-$ into the differential amplifier $A_3$ shown in FIG. 1 must be switched on both sides of the line of $\lambda = 1$ as shown in FIG. 6. If $r > r_2$ in FIG. 1, the temperature of the air-fuel ratio detecting cell 1 is low, so that it is necessary to heat the detecting cell 1 by the built-in heater. The pumping current Ip in a lean region flows from Vo to $V_{PG}$. Consequently, the outputs $e^+$, $e^-$ from the bridge circuit become $e^+ > e^-$, and the differential amplifier $A_3$ generates a high-level output signal, an electric current being supplied to the heater to heat the cell 1. Conversely, the pumping current Ip in the rich region flows from $V_{PG}$ to Vo. Therefore, when $r > r_2$, the outputs $e^+$, $e^-$ from the bridge circuit become $e^+ < e^-$, so that the heating of the cell 1 cannot be done. This makes it necessary to provide a change-over means for reversing the polarity of an input into the differential amplifier $A_3$ in the rich region.

The temperature control unit shown in FIG. 1 is formed so as to detect an air-fuel ratio in a lean region alone, and unsuitable to be used for controlling the temperature in all air-fuel ratio regions. The embodiment of FIG. 6 does not use a switch as a change-over means for reversing the polarity of an input into the differential amplifier $A_3$ unlike the previously-described embodiment but it is formed so that the controlling of the temperature can be done continuously.

Referring to FIG. 6, reference letters $B_1$, $B_2$, $B_3$, $B_4$ denote open collector type comparators, $D_1$, $D_2$ diodes, and $R_{S1}$, $R_{S2}$, Rb, Ra resistors, the same reference numerals and letters as shown in FIG. 1 denoting the same parts as shown therein. The operations in the embodiment of FIG. 6 except the temperature controlling operation thereof are identical with those described previously, and the descriptions of the operations will be omitted.

When the output signals $e^+$, $e^-$ from the bridge circuit are switched in the rich and lean regions, the comparators $B_1$, $B_2$ are used. The comparators $B_1$, $B_2$ output "High" or "Low" signals in accordance with the level of the signals $e^+$, $e^-$.

In the comparators $B_3$, $B_4$, Vref corresponding to the value of Vo attained when $\lambda = 1$ is input into one input terminal, and the value of Vo into the other input terminal. In accordance with the level of the input signal of Vo, a "High" or "Low" signal is output from the output terminals of the comparators $B_3$, $B_4$. When a "High" signal is output from the comparator $B_3$, $\lambda > 1$, and, conversely, when a "High" signal is output from the comparator $B_4$, $\lambda < 1$.

Therefore, an AND-circuit consisting of the comparators $B_1$, $B_3$, and resistor $R_{S1}$, and an AND-circuit consisting of the comparators $B_2$, $B_4$ and resistor $R_{S2}$ are formed. The level of the outputs from these AND-circuits becomes "High" when both of $B_1$, $B_3$ have become "High" in the lean region or when both of $B_2$, $B_4$ have become "High" in the rich region.

An OR-circuit consisting of $D_1$, $D_2$, Tr is adapted to supply an electric current to the heater 3 when either of the two AND-circuits has become "High", to heat the air-fuel ratio detecting cell 1. Conversely, when either of the AND-circuits is in a "Low" level, the supplying of the electric current to the heater 3 is interrupted.

These operations are repeated, so that the heater 3 is heated and cooled (with the natural cold heat in this case). Consequently, the internal resistance, i.e. the temperature of the air-fuel ratio detecting cell 1 is controlled to a constant level.

According to the above-described arrangement, a temperature controlling operation can be carried out continuously in all air-fuel ratio regions.

The above-described method is carried out with the electromotive force control value e kept constant. If e is set variable, the temperature of the air-fuel ratio detecting cell 1 can be controlled to a lower level, and the reducing of the electric power required by the heater and the improving of the low-temperature operation efficiency can be done effectively.

Figure 7:
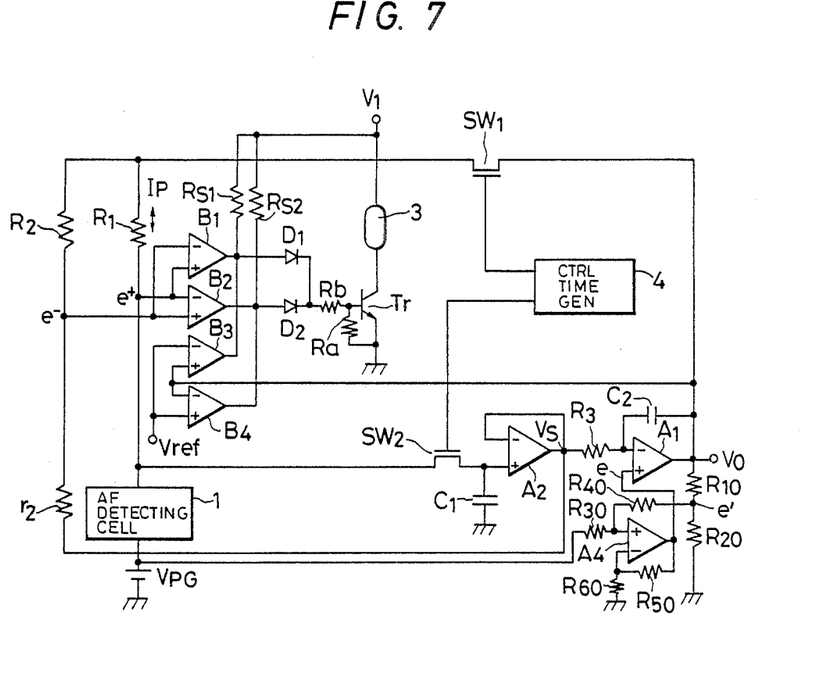
FIG. 7 shows an example of an electromotive force controlling variable type air-fuel ratio detector.

Referring to FIG. 7, in order to variably control the electromotive force control value, resistors $R_{10}$, $R_{20}$, $R_{30}$, $R_{40}$, $R_{50}$, $R_{60}$ and a differential amplifier $A_4$ may be added. Since the operations except the operations of these parts are identical with those described previously with reference to FIGS. 1 and 6, the description thereof will be omitted.

An electromotive force control value e', which is obtained by dividing an output voltage Vo varying in accordance with an excessive air ratio $\lambda$ by the resistors $R_{10}$, $R_{20}$, is input into one input terminal of an adder consisting of $R_{30}$–$R_{60}$ and $A_4$. When a value of $V_{PG}$ is input into the other input terminal, an output from the differential amplifier $A_4$ at this time, i.e. an electromotive force control value e can be expressed by the following equation.

$$e = (R_{50}/R_{100})(V_{PG} + e') \quad (8)$$

wherein $R_{100}=R_{30}=R_{40}=R_{60}$. Accordingly, if $R_{50}=R_{100}$, $e=V_{PG}+e'$, and e' alone varies with Vo. Therefore, the electromotive force control value e substantially varies. The electromotive force control value e' at this time may be set so that it is about 0.2–0.3 V when $\lambda=0.5$, and about 0.6–0.7 V when $\lambda=1.5$. The circuit shown in FIG. 7 is advantageously used to determine the air-fuel ratio in an exhaust gas in which the quantity of the air has increased temporarily due to the air flowing into the exhaust gas after, for example, an interruption in the supplying of fuel into the engine.

Figure 8:
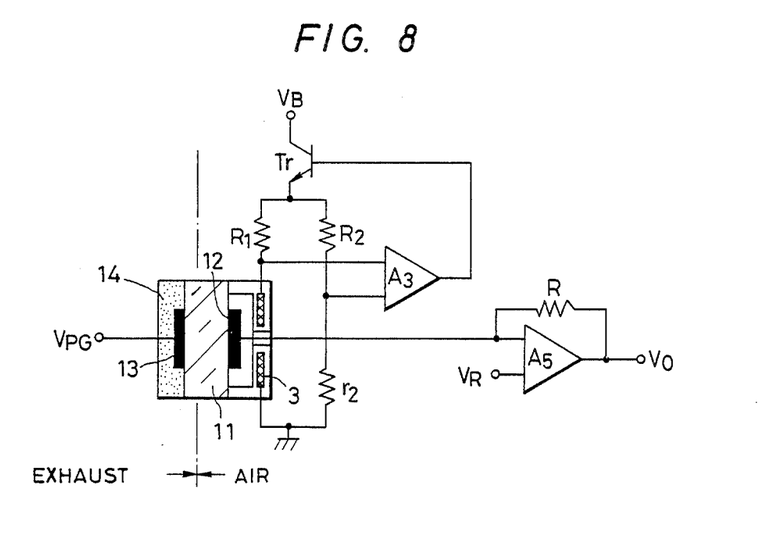
FIGS. 8 and 9 show applied examples of the present invention.

A plate type heater-containing air-fuel ratio detecting cell shown in FIG. 8 is formed by unitarily combining a cell member with the heater, and enables the temperature control method and the circuit structure thereof to be simplified, so that this detecting cell can be miniaturized. The elements 3, 11, 12, 13, 14 shown in FIG. 8 correspond to those 3', 11', 12', 13', 14', respectively, shown in FIG. 2. Among these elements, the heater 3 consists, for example, of a platinum heater. Accordingly, if the temperature dependency of the resistance value RH of the heater 3 due to the platinum is determined, a bridge circuit is formed by the resistors $R_1$, $R_2$, $r_2$ shown in the drawing, and this circuit may be controlled by a differential amplifier $A_3$ and a transistor Tr so that the equilibrium conditions expressed by the following equation can be met.

$$R_1/RH = R_2/r_2 \qquad (9)$$

Therefore, it is not necessary to form a modified bridge circuit according to the present invention to which an electromotive force is applied. This enables the circuit to be simplified, the heat radiation rate to be minimized, and the detection accuracy to be improved easily.

Figure 9:
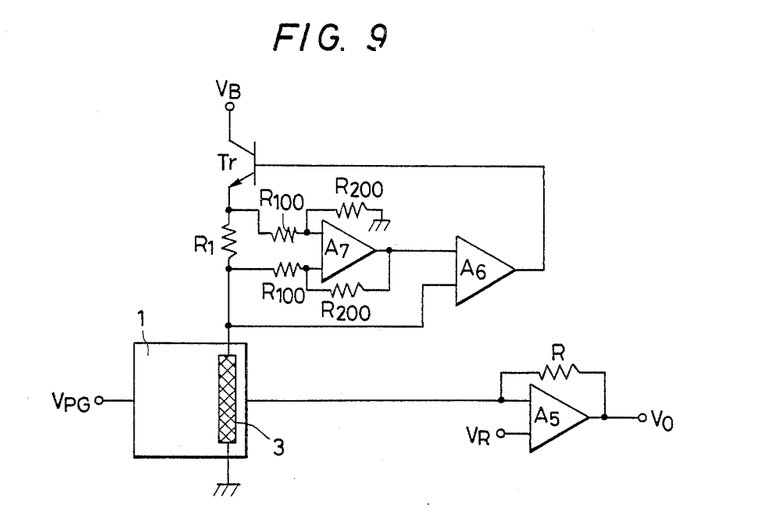

Referring to FIG. 9, reference letters $R_{100}$, $R_{200}$ denote resistors, and $A_6$, $A_7$ differential amplifiers, the other reference numerals and letters denoting the same elements as the same reference numerals and letters shown in FIG. 8.

In this method, the heater current $I_H$ is supplied to the resistor $R_1$ and a heater 3 through the transistor Tr so that the degree of voltage drop at the resistor $R_1$ and that of voltage drop at the heater 3 become equal. Let $R_H$ equal the resistance value of the heater 3 to be controlled. The voltage drop $V_{R1}$, $V_{RH}$ at $V_{R1}$, $V_{RH}$ can be expressed by the following equations.

$$V_{R1} = I_H \cdot R_1 \qquad (10)$$

$$V_{RH} = I_H \cdot R_H \qquad (11)$$

In the differential amplifier $A_7$, $V_{R1}$ is detected, and a control operation is carried out so that the equations (10), (11) become equal at $A_6$. Consequently, $V_{R1}$ becomes equal to $V_{RH}$. Accordingly, $R_1$, $R_H$ are controlled to be equal irrespective of the heater current $I_H$.

Therefore, a resistance value $R_1$ equal to a desired $R_H$ may be set on the basis of the temperature dependency of the resistance value $R_H$ of the platinum heater 3. In order to prevent the generation of heat at $R_1$, $R_I$ is set small so as to increase the gain of the differential amplifier $A_7$ accordingly. As a result, the same effect as described in the statement of the embodiment of FIG. 8 can be obtained.

What is claimed is:

1. An air-fuel ratio detector, comprising:

an air-fuel ratio detecting cell (1) for detecting an air-fuel ratio from components of an exhaust gas of an automobile, an electric current detecting resistor (R) and a switching element (SW) connected in series between said detecting cell (1) and a power source (Vo), a sample hold circuit ($SW_2$, $C_1$, $A_2$) for sample-holding an output voltage from said detecting cell (1) when said switching element is turned off, comparator means ($A_1$) for comparing an output from said sample hold circuit with an electromotive force control value (e), a temperature setting resistor ($r_2$) and a load resistor ($R_2$) connected in series between an output terminal of said sample hold circuit and said switching element, and a differential amplifier ($A_3$) to which voltages ($e^+$, $e^-$) respectively from a node of said detecting cell and said electric current detecting resistor and a node of said temperature setting resistor and said load resistor are supplied, said air-fuel ratio detector further including a potential ground ($V_{PG}$) connected to a cathode of said detecting cell, and means (Tr) for controlling an electric current flowing into a heater contained in said detecting cell, on the basis of an output from said differential amplifier and thereby controlling internal resistance (r) of said detecting cell to a predetermined level.

2. An air-fuel ratio detector according to claim 1, wherein a voltage of said power source is supplied from an output terminal of said comparator means.

3. An air-fuel ratio detector according to claim 2, wherein said differential amplifier comprises:

a first group of two comparators ($B_1$, $B_2$) connected complementarily to said voltages and adapted to output a "High" or "Low" signal in accordance with the level of said voltages, said differential amplifier being further provided with a second group of two complementarily-connected comparators ($B_3$, $B_4$) adapted to receive at one input terminal a voltage (Vref) which corresponds to an output voltage from said comparator means (A1) when an excess air ratio is 1, and at another input terminal to receive an output voltage (Vo) from said comparator means (A1), and to output a "High" or "Low" signal in accordance with the level of said output voltage (Vo), a first AND-circuit adapted to carry out an AND-operation, said first AND-circuit including a first one of said comparators ($B_1$) included in said first group of comparators and adapted to output a "High" signal in accordance with the level of said voltages, and a second one of said comparators ($B_3$) included in said second group of comparators and adapted to output a "High" signal in accordance with the level of said output voltage, a second AND-circuit adapted to carry out an AND-operation, said second AND-circuit including a first one of said comparators ($B_2$) included in said first group of comparators and adapted to output "High" signal in accordance with the level of said voltages and a second one of said comparators ($B_4$) included in said second group of comparators and adapted to output a "High" signal in accordance with the level of said output voltage, and means ($D_1$, $D_2$) for operating said electric current control means (Tr) on the basis of an output signal from either of said first and second AND-circuits.

4. An air-fuel ratio detector according to claim 3, further comprising means connected between said comparator means, said power source and said potential ground for controlling said electromotive force control value (e).

5. An air-fuel ratio detector according to claim 4, wherein said means for controlling said electromotive force control value (e) comprises an adder.

6. An air-fuel ratio detector according to claim 4, wherein said means for controlling said electromotive force control value comprises:
   a first resistor coupled to a reference potential;
   a second resistor coupled between said first resistor and a first input terminal of said comparator means;
   means for dividing a potential between said power source and said reference potential;
   third and fourth resistors serially coupled between said potential ground and said dividing means; and
   adder means having a first input terminal coupled to a node between said first and second resistors, a second input terminal coupled to a node between said third and fourth resistors, and an output terminal coupled to said first input terminal of said comparator means, for providing to said first input terminal of said comparator means said electromotive force control value (e) varying with the value of a voltage of said power source.

7. An air-fuel ratio detector according to claim 6, wherein the values of the resistances of said first, second, third and fourth resistors are approximately equal.

8. An air-fuel ratio detector according to claim 3, wherein said comparator means comprises:
   a first resistor coupling said output of said sample hold circuit to one input terminal of said comparator means; and
   a first capacitance coupled between said one input terminal and an output terminal of said comparator means.

9. An air-fuel ratio detector according to claim 8, further comprising:
   a second resistor coupled to a reference potential;
   a third resistor coupled between said second resistor and a second input terminal of said comparator means;
   means for dividing a potential between said power source and said reference potential;
   fourth and fifth resistors serially coupled between said potential ground and said dividing means; and
   adder means having a first input terminal coupled to a node between said second and third resistors, a second input terminal coupled to a node between said fourth and fifth resistors, and an output terminal coupled to said second input terminal of said comparator means, for providing to said second input terminal of said comparator means said electromotive force control value (e) varying with the value of a voltage of said power source.

10. An air-fuel ratio detector according to claim 9, wherein the values of the resistances of said second, third, fourth and fifth resistors are approximately equal.

11. An air-fuel ratio detector according to claim 1, wherein said comparator means comprises:
    a first resistor coupling said output of said sample hold circuit to one input terminal of said comparator means; and
    a first capacitance coupled between said one input terminal and an output terminal of said comparator means.

12. An air-fuel ratio detector according to claim 11, further comprising:
    a second resistor coupled to a reference potential;
    a third resistor coupled between said second resistor and a second input terminal of said comparator means;
    means for dividing a potential between said power source and said reference potential;
    fourth and fifth resistors serially coupled between said potential ground and said dividing means; and
    adder means having a first input terminal coupled to a node between said second and third resistors, a second input terminal coupled to a node between said fourth and fifth resistors, and an output terminal coupled to said second input terminal of said comparator means, for providing to said second input terminal of said comparator means said electromotive force control value (e) varying with the value of a voltage of said power source.

13. An air-fuel ratio detector according to Claim 12, wherein the values of the resistances of said second, third, fourth and fifth resistors are approximately equal.

14. An air-fuel ratio detector according to claim 1, further comprising means connected between said comparator means, said power source and said potential ground for controlling said electromotive force control value.

15. An air-fuel ratio detector according to claim 14, wherein said means for controlling said electromotive force control value (e) comprises an adder.

16. An air-fuel ratio detector circuit usable with an air-fuel ratio detecting cell for detecting an air-fuel ratio from components of an exhaust gas of an automobile, comprising:
    an electric current detecting resistor connected between a heater contained in said detecting cell and a first node;
    a temperature setting resistor and a load resistor connected in series between said heater and said first node;
    a differential amplifier to which voltages ($e^+$, $e^-$) from a second node between said heater and said electric current detecting resistor and a third node between said temperature setting resistor and said load resistor are supplied;
    a cathode of said detecting cell being connected to a potential ground; and
    means for controlling an electric current flowing into the heater on the basis of an output from said differential amplifier and thereby controlling internal resistance of the detecting cell to a predetermined level.

17. An air-fuel ratio detector according to claim 16, further comprising:
    means for coupling said first node to a power source;
    sample-holding means connecting said third node and said temperature setting resistor, for holding an output voltage from a detecting cell when said couplding means is in a non-electrically conducting condition; and
    comparator means disposed between said temperature setting resistor and said third node, for making a comparison between an output from said sample-holding means and an control value, and for regulating electric current passing through said electric current detecting resistor on the basis of the comparison.

18. An air-fuel ratio detector according to claim 17, wherein said differential amplifier comprises;
   a first group of two comparators connected complimentarily to said voltages and adapted to provide a logical "High" or "Low" signal in accordance with the level of said voltages;
   a second group of two complimentarily-connected comparators adapted to receive at one input terminal a reference voltage corresponding to an output voltage from said comparator means when an excess air ratio is ONE and at another input terminal to receive an output voltage from said comparator means, and to provide a logical "High" or "Low" signal in accordance with the level of said output voltage;
   a first AND-circuit adapted to perform an AND-operation, said first AND circuit including a first one of said comparators included in said first group of comparators adapted to provide a logical "High" signal in accordance with the level of said voltages, and a second one of said comparators included in said second group of comparators and adapted to provide a logical "High" signal in accordance with the level of said output voltage;
   a second AND-circuit adapted to perform an AND-operation, said second AND-circuit including a first one of said comparators included in said first group of comparators adapted to provide a logical "High" signal in accordance with the level of said voltages, and a second one of said comparators included in said second group of comparators and adapted to provide a logical "High" signal in accordance with a level of said output voltages; and
   means for operating said controlling means on the basis of an output signal from either of said first and second AND-circuits.

19. An air-fuel ratio detector according to claim 18, wherein said comparator means comprises:
   a first resistor coupling said output from said sample-holding means to one input terminal of said comparator means; and
   a first capacitor coupled between said one input terminal and an output terminal of said comparator means.

20. An air-fuel ratio detector according to claim 19, further comprising:
   a second resistor coupled to a reference potential;
   a third resistor coupled between said second resistor and a second input terminal of said comparator means;
   means for dividing a potential between said power source and said reference potential;
   fourth and fifth resistors serially coupled between said potential ground and said dividing means; and
   adder means having a first input terminal coupled between said second and third resistors, a second input terminal coupled between said fourth and fifth resistors, and an output terminal coupled to said second input terminal of said comparator means, for providing to said second input terminal of said comparator means an electromotive force control value varying with the value of a voltage of said power source.

21. An air-fuel ratio detector according to claim 20, wherein the values of the resistances of said second, third, fourth and fifth resistors are approximately equal.

22. An air-fuel ratio detector, comprising:
   an air-fuel ratio detecting cell including a cathode and a heater;
   a first impedance extending between a first and a second node;
   a second impedance extending between said second node and a third node;
   a third impedance extending between said third node and a fourth node;
   means connected between said first and third nodes for controlling an electric current flowing into said heater on the basis of any potential difference between said first and third nodes;
   means for coupling said second node to a power source;
   sample-holding means connecting said first node and said third impedance, for holding an output voltage from said detecting cell when said coupling means is in a non-electrically conducting condition; and
   comparator means disposed between said third impedence and said first node, and separated by said third impedance from said third node for making a comparison between an output from said sample-holding means and a control value, and for regulating electric current passing through said first impedance on the basis of the comparison.

23. An air-fuel ratio detector according to claim 22, wherein said controlling means comprises:
   a first group of two comparators connected complimentarily to voltages respectively supplied from said first node and said third node, and adapted to provide a logical "High" or "Low" signal in accordance with the level of said voltages;
   a second group of two complimentarily-connected comparators adapted to receive at one input terminal a reference voltage corresponding to an output voltage from said comparator means when an excess air ratio is ONE, and at another input terminal to receive an output voltage from said comparator means, and provide a logical "High" or "Low" signal in accordance with the level of said output voltage;
   a first AND-circuit adapted to provide an AND-operation, said first and-circuit including a first one of said comparators included in said first group of comparators adapted to provide a logical "High" signal in accordance with the level of said voltages, and a second one of said comparators included in said second group of comparators and adapted to provide a logical "High" signal in accordance with the level of said output voltage;
   a second AND-circuit adapted to perform an AND-operation, said AND-circuit including a first one of said comparators included in said first group of comparators and adapted to provide a logical "High" signal in accordance with a level of said voltages, and a second one of said comparators included in the said second group of comparators and adapted to provide a logical "High" signal in accordance with the level of said voltage;
   means connected to said second node for regulating the amplitute of said electric current flowing into said heater; and
   means for operating said regulator means on the basis of an output signal from either of said first and second circuits.

24. An air-fuel ratio detector according to claim 22, wherein said comparator means comprises:

a first resistor coupling said output of said sample-holding means to one input terminal of said comparator means; and a first capacitor coupled between one input terminal and an output terminal of said comparator means.

25. An air-fuel ratio detector according to claim 24, further comprising:

a second resistor coupled to a reference potential;

a third resistor coupled between second resistor and a second input terminal of said comparator means;

means for dividing a potential between said power source and said reference potentials;

fourth and fifth resistors serially coupled between said potential ground and said dividing means; and adder means having a first input terminal coupled to a junction between said second and third resistors, a second input terminal coupled to a junction between said fourth and fifth resistors, and an output terminal coupled to said second input terminal of said comparator means, for providing to said second input terminal of said comparator means a control value varying with the value of a voltage of said power source.

26. An air-fuel ratio detector according to claim 25, wherein the values of the resistances of said second, third, fourth and fifth resistors are approximately equal.

* * * * *